(12) United States Patent
Kim et al.

(10) Patent No.: US 11,248,246 B2
(45) Date of Patent: Feb. 15, 2022

(54) BETA-GLUCOSIDASE FOR PRODUCING GLUCOSE AND LAMINARIOLIGOSACCHARIDE FROM SEA WEED

(71) Applicant: Korea University Research and Business Foundation, Seoul (KR)

(72) Inventors: Kyoung Heon Kim, Seoul (KR); Dong-Hyun Kim, Busan (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/979,568

(22) PCT Filed: Mar. 8, 2019

(86) PCT No.: PCT/KR2019/002706
§ 371 (c)(1),
(2) Date: Sep. 10, 2020

(87) PCT Pub. No.: WO2019/177311
PCT Pub. Date: Sep. 19, 2019

(65) Prior Publication Data
US 2021/0040522 A1    Feb. 11, 2021

(30) Foreign Application Priority Data

Mar. 12, 2018 (KR) .................. 10-2018-0028510

(51) Int. Cl.
| | |
|---|---|
| *C12P 19/02* | (2006.01) |
| *C12P 19/04* | (2006.01) |
| *C12P 19/14* | (2006.01) |
| *C12P 19/18* | (2006.01) |
| *C12N 9/42* | (2006.01) |

(52) U.S. Cl.
CPC .............. *C12P 19/02* (2013.01); *C12N 9/2445* (2013.01); *C12P 19/04* (2013.01); *C12P 19/14* (2013.01); *C12P 19/18* (2013.01); *C12Y 302/01* (2013.01)

(58) Field of Classification Search
None
See application file for complete search history.

(56) References Cited

U.S. PATENT DOCUMENTS

2021/0040522 A1*  2/2021  Kim .................. C12P 19/14

FOREIGN PATENT DOCUMENTS

| KR | 10-2017-0124149 A | 11/2017 |
|---|---|---|
| KR | 10-1784665 B1 | 11/2017 |

OTHER PUBLICATIONS

UniProt Accession No. Q21KX3_SACD2, published Apr. 18, 2006 (Year: 2006).*

(Continued)

*Primary Examiner* — Richard C Ekstrom
(74) *Attorney, Agent, or Firm* — Sughrue Mion, PLLC

(57) ABSTRACT

The present invention relates to a novel beta-glucosidase for producing glucose and a laminarioligosaccharide from seaweed. More particularly, the present invention may produce glucose from a beta-glucosidase exhibiting transglycosylase activity while showing exo-type glucanase activity against beta-glucan, as well as produce a laminarioligosaccharide by exhibiting transglycosylase activity against laminarin under different reaction conditions.

2 Claims, 9 Drawing Sheets
Specification includes a Sequence Listing.

(56) References Cited

OTHER PUBLICATIONS

Kim et al., "A novel beta-glucosidase from Saccharophagus degradans 2-40T for the efficient hydrolysis of laminarin from brown macroalgae", Biotechnology for Biofuels, vol. 11, p. 64, published Mar. 14, 2018 (Year: 2018).*

Brognaro et al., "Biochemical characterization and low-resolution SAXS molecular envelope of GH1 beta-glucosidase from Saccharophagus degradans", Molecular Biotechnology, vol. 58, pp. 777-788, published Sep. 26, 2016 (Year: 2016).*

NCBI GenBank Accession No. WP_011467876.1, May 12, 2016.

Wenming Zhang et al., Purification, characterization and function analysis of an extracellular β-glucosidase from elongating stipe cell walls in Coprinopsis cinerea, FEMS Microbiology Letters, 2016, 9pages, vol. 363, No. 9.

Keisuke Motone et al., "Direct ethanol fermentation of the algal storage polysaccharide laminarin with an optimized combination of engineered yeasts", Journal of Biotechnology, 2016, pp. 129-135, vol. 231.

International Search Report for PCT/KR2019/002706 dated Jun. 19, 2019 [PCT/ISA/210].

* cited by examiner

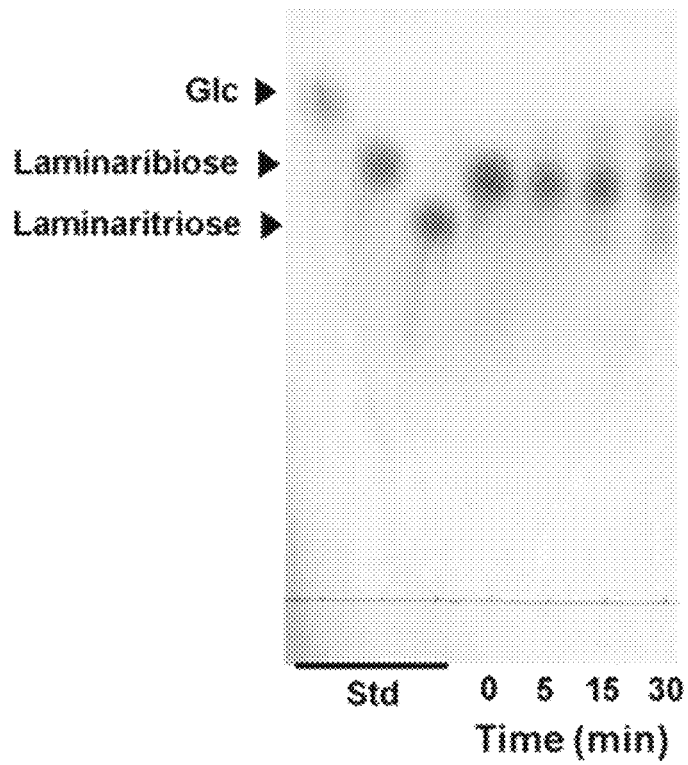

FIG. 8C

Nucleotide sequences of Bgl1B

Atgaatagacttacactaccgccttcttctcgtttgcgcagcaaagagtttacctttggtgttgcaacgtcgtcttaccaaattgaaggcggcatag
attctcGcctgccctgtaattgggatacgttctgtgagcagcccaataccattatigataacaccaacggcgccattgctigcgaccacataaatag
atggcaagaCgatatagaacttattgccaacctaggggtagatgcctaccgcttttctattgcgtgggcCgtgttattaatttagacggcagcct
caataatgaaggcgTtacattttacaaaaatatttttaactaagcttcgcgaaaagaatttaaaagcttatataacgctataccactgggacttgcca
caacatttagaagatgctggCggctggcttaaccgcgataccgcctacaagtttcgcgactatgtaaaccttataacccaagcgcttgatgacga
tgtattttgctacacaacgttaaacgaGcccttttgcagtgcctacctggctatgaaattggtgtacacgcaccgggtataaaagacttagccagt
gggcgcaaagccgcacaccatttattacttgCccatggcttagctatgcaagtgctgcgaaaaaactgcccaatagtttaagcggcatagtgtt
aaacatgagcccttgttacgccggcagcaacgcacaAgcagatatagatgcagcaaaacgcgcggacgatttattatttcagtggtatgcacaa
ccgctacttactggctgctaccctgatgcaataaaacagcctgcCagacaatgccaaaccacctatttgtgaaggcgacatggcgttaataagcca
accttagattatttaggccttaactactataccogcgcagtatttttgccGacggtaatggcggtttaccgaacaagtacctgagggtgtagag
ctaaccgatatgggctgggaagtttacccgcaaggcttaaccgattiactaatagAcctaaaccaacgctatacctaccccgttacttattaccg
aaaacggcgcagcaatggtggacgaacttgttaacggcgaagttaacgatattgcccgaAtaaattattttcaaacccatttacaagcggtacac
aacgccattgaacaaggtgttgatgtacgcggttattttgcttggagcctaatggataattttgagtgGgcactgggttacagcaaacgattcgg
tattacctatgtagattaccaaacacaaaagcgaacgctaaaagccagcggccacgcatttgctgagtttgtctcgagtaggagctaa

SEQUENCE LISTING

<160> NUMBER OF SEQ ID NOS: 4

<210> SEQ ID NO 1
<211> LENGTH: 444
<212> TYPE: PRT
<213> ORGANISM: Saccharophagus degradans 2-40T

<400> SEQUENCE: 1

```
Met Asn Arg Leu Thr Leu Pro Pro Ser Ser Arg Leu Arg Ser Lys Glu
1               5                   10                  15

Phe Thr Phe Gly Val Ala Thr Ser Ser Tyr Gln Ile Glu Gly Gly Ile
            20                  25                  30

Asp Ser Arg Leu Pro Cys Asn Trp Asp Thr Phe Cys Glu Gln Pro Asn
        35                  40                  45

Thr Ile Ile Asp Asn Thr Asn Gly Ala Ile Ala Cys Asp His Ile Asn
    50                  55                  60

Arg Trp Gln Asp Asp Ile Glu Leu Ile Ala Asn Leu Gly Val Asp Ala
65                  70                  75                  80

Tyr Arg Phe Ser Ile Ala Trp Gly Arg Val Ile Asn Leu Asp Gly Ser
                85                  90                  95
```

Leu Asn Asn Glu Gly Val Thr Phe Tyr Lys Asn Ile Leu Thr Lys Leu
            100                 105                 110

Arg Glu Lys Asn Leu Lys Ala Tyr Ile Thr Leu Tyr His Trp Asp Leu
        115                 120                 125

Pro Gln His Leu Glu Asp Ala Gly Gly Trp Leu Asn Arg Asp Thr Ala
    130                 135                 140

Tyr Lys Phe Arg Asp Tyr Val Asn Leu Ile Thr Gln Ala Leu Asp Asp
145                 150                 155                 160

Asp Val Phe Cys Tyr Thr Thr Leu Asn Glu Pro Phe Cys Ser Ala Tyr
                165                 170                 175

Leu Gly Tyr Glu Ile Gly Val His Ala Pro Gly Ile Lys Asp Leu Ala
            180                 185                 190

Ser Gly Arg Lys Ala Ala His His Leu Leu Leu Ala His Gly Leu Ala
        195                 200                 205

Met Gln Val Leu Arg Lys Asn Cys Pro Asn Ser Leu Ser Gly Ile Val
    210                 215                 220

Leu Asn Met Ser Pro Cys Tyr Ala Gly Ser Asn Ala Gln Ala Asp Ile
225                 230                 235                 240

Asp Ala Ala Lys Arg Ala Asp Leu Leu Phe Gln Trp Tyr Ala Gln
                245                 250                 255

Pro Leu Leu Thr Gly Cys Tyr Pro Asp Ala Ile Asn Ser Leu Pro Asp
            260                 265                 270

Asn Ala Lys Pro Pro Ile Cys Glu Gly Asp Met Ala Leu Ile Ser Gln
        275                 280                 285

Pro Leu Asp Tyr Leu Gly Leu Asn Tyr Tyr Thr Arg Ala Val Phe Phe
    290                 295                 300

Ala Asp Gly Asn Gly Gly Phe Thr Glu Gln Val Pro Glu Gly Val Glu
305                 310                 315                 320

Leu Thr Asp Met Gly Trp Glu Val Tyr Pro Gln Gly Leu Thr Asp Leu
                325                 330                 335

Leu Ile Asp Leu Asn Gln Arg Tyr Thr Leu Pro Pro Leu Leu Ile Thr
            340                 345                 350

Glu Asn Gly Ala Ala Met Val Asp Glu Leu Val Asn Gly Glu Val Asn
        355                 360                 365

Asp Ile Ala Arg Ile Asn Tyr Phe Gln Thr His Leu Gln Ala Val His
    370                 375                 380

Asn Ala Ile Glu Gln Gly Val Asp Val Arg Gly Tyr Phe Ala Trp Ser
385                 390                 395                 400

Leu Met Asp Asn Phe Glu Trp Ala Leu Gly Tyr Ser Lys Arg Phe Gly
                405                 410                 415

Ile Thr Tyr Val Asp Tyr Gln Thr Gln Lys Arg Thr Leu Lys Ala Ser
            420                 425                 430

Gly His Ala Phe Ala Glu Phe Val Ser Ser Arg Ser
        435                 440

<210> SEQ ID NO 2
<211> LENGTH: 1335
<212> TYPE: DNA
<213> ORGANISM: Saccharophagus degradans 2-40T

<400> SEQUENCE: 2
atgaatagac ttacactacc gccttcttct cgtttgcgca gcaaagagtt tacctttggt    60
gttgcaacgt cgtcttacca aattgaaggc ggcatagatt ctcgcctgcc ctgtaattgg   120
gatacgttct gtgagcagcc caataccatt attgataaca ccaacggcgc cattgcttgc   180

```
gaccacataa atagatggca agacgatata gaacttattg ccaacctagg ggtagatgcc    240
taccgctttt ctattgcgtg gggccgtgtt attaatttag acggcagcct caataatgaa    300
ggcgttacat tttacaaaaa tattttaact aagcttcgcg aaaagaattt aaaagcttat    360
ataacgctat accactggga cttgccacaa catttagaag atgctggcgg ctggcttaac    420
cgcgataccg cctacaagtt tcgcgactat gtaaacctta taacccaagc gcttgatgac    480
gatgtatttt gctacacaac gttaaacgag ccctttttgca gtgcctacct tggctatgaa    540
attggtgtac acgcaccggg tataaaagac ttagccagtg ggcgcaaagc cgcacaccat    600
ttattacttg cccatggctt agctatgcaa gtgctgcgaa aaaactgccc caatagttta    660
agcggcatag tgttaaacat gagcccttgt tacgccggca gcaacgcaca agcagatata    720
gatgcagcaa aacgcgcgga cgatttatta tttcagtggt atgcacaacc gctacttact    780
ggctgctacc ctgatgcaat aaacagcctg ccagacaatg ccaaaccacc tatttgtgaa    840
ggcgacatgg cgttaataag ccaacctta gattatttag gccttaacta ctatacccgc    900
gcagtatttt ttgccgacgg taatggcggt tttaccgaac aagtacctga gggtgtagag    960
ctaaccgata tgggctggga agtttacccg caaggcttaa ccgatttact aatagaccta    1020
aaccaacgct ataccctacc cccgttactt attaccgaaa acggcgcagc aatggtggac    1080
gaacttgtta acgcgaagt taacgatatt gcccgaataa attattttca aacccattta    1140
caagcggtac acaacgccat tgaacaaggt gttgatgtac gcggttattt tgcttggagc    1200
ctaatggata atttgagtg ggcactgggt tacagcaaac gattcggtat tacctatgta    1260
gattaccaaa cacaaaagcg aacgctaaaa gccagcggcc acgcatttgc tgagtttgtc    1320
tcgagtagga gctaa                                                    1335

<210> SEQ ID NO 3
<211> LENGTH: 39
<212> TYPE: DNA
<213> ORGANISM: Artificial Sequence
<220> FEATURE:
<223> OTHER INFORMATION: Forward primer for bgl1B amplification

<400> SEQUENCE: 3
atacatatga atagacttac actaccgcct tcttctcgt                           39

<210> SEQ ID NO 4
<211> LENGTH: 41
<212> TYPE: DNA
<213> ORGANISM: Artificial Sequence
<220> FEATURE:
<223> OTHER INFORMATION: Reverse primer for bgl1B amplification

<400> SEQUENCE: 4
atagcggccg cgctcctact cgagacaaac tcagcaaatg c                        41
```

BETA-GLUCOSIDASE FOR PRODUCING GLUCOSE AND LAMINARIOLIGOSACCHARIDE FROM SEA WEED

CROSS REFERENCE TO RELATED APPLICATIONS

This application is a National Stage of International Application No. PCT/KR2019/002706 filed Mar. 8, 2019, claiming priority based on Korean Patent Application No. 10-2018-0028510 filed Mar. 12, 2018, the entire disclosures of which are incorporated herein by reference.

BACKGROUND

1. Field of the Invention

The present invention relates to a novel β-glucosidase for producing glucose and a laminarioligosaccharide from seaweed.

2. Discussion of Related Art

Along with concerns on global warming, interest in renewable biomass for sustainable development has been increasing. Lignocellulosic biomass has long been considered as renewable biomass for producing fermentable sugars such as glucose due to abundant resources and low cost. However, it has a high content of lignin and a very complicated structure, and thus requires high-strength pretreatment and enzymatic glycosylation, making it difficult to use. Recently, seaweed has received much attention as biomass which replaces lignocellulosic biomass, and is advantageous in terms of high carbohydrate contents, no need for arable land, and an uncomplicated structure due to almost no lignin content.

Among marine algae, about 70 million tons of brown algae are harvested annually worldwide, the main carbohydrate components of brown algae are alginic acid and a glucan, and the glucan is mainly laminarin. Laminarin has β-1,3 linkages in a backbone thereof and β-1,6 linkages in branches thereof. Among brown algae, *Laminarina, Saccharina* and *Fucus* spp. have a high laminarin content of 30-80% dry weight. Since laminarin is a polysaccharide consisting of glucose, laminarin is very ideal biomass for producing fermentable sugars. In addition, laminarioligosaccharides produced from laminarin are known to have various physiological activities, and thus can be used as a functional material.

To produce fermentable sugars using lignocellulosic biomass, high-strength pretreatment is required, and it requires a combination of at least three enzymes such as endoglucanase, exo-glucanase, and beta-glycosidase. Such a pretreatment process uses high heat, and thus requires much energy, and the cost of enzymes used in an enzymatic glycosylation process accounts for a very large portion of an overall bioprocess.

Therefore, there is a need for a process for producing glucose, which is a fermentation sugar, and laminarioligosaccharides, which are a functional material, by efficiently hydrolyzing laminarin, at reduced production costs by using a minimum number of enzymes.

SUMMARY OF THE INVENTION

An object of the present invention is to provide a use of a novel β-glucosidase for producing glucose and a laminarioligosaccharide from brown algae.

According to an aspect of the present disclosure, there is provided a composition for producing glucose or a laminarioligosaccharide, including a β-glucosidase having the amino acid sequences of SEQ ID NO: 1, wherein the β-glucosidase has exo-type glucanase and transglycosylase activities.

The present invention also provides a method of producing glucose or a laminarioligosaccharide, including reacting a β-glucosidase having the amino acid sequences of SEQ ID NO: 1 with laminarin or laminaribiose to thereby produce glucose or a laminarioligosaccharide.

A β-glucosidase of the present invention exhibits exo-type glucanase activity against laminarin, which is a polysaccharide, and thus produces only glucose, and also exhibits transglycosylase activity against laminarin or laminaribiose by varying reaction conditions, and thus has the effect of producing glucose and/or a laminarioligosaccharide.

BRIEF DESCRIPTION OF THE DRAWINGS

6A illustrates a yield of glucose produced as a major product by hydrolyzing laminarin.

FIG. 8B illustrates TLC analysis results of laminaritriose and glucose, and FIG. 8C shows the nucleotide sequence (SEQ ID NO: 2) of Bgl1B.

DETAILED DESCRIPTION OF EXEMPLARY EMBODIMENTS

Figure 1:
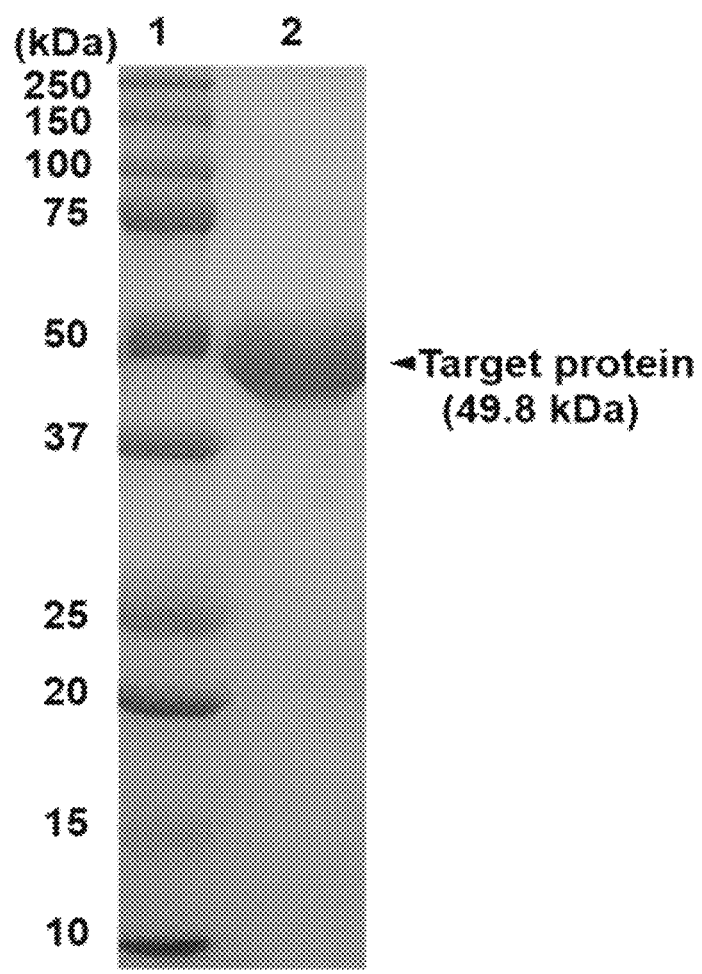
FIG. 1 is a gel image confirming the expression of a β-glucosidase of the present invention.

The inventors of the present invention examined the laminarin degradation activity of the Bgl1B protein, which is assumed to have β-glucosidase activity. As a result, it was confirmed that the Bgl1B protein cleaved, through exo-type glucanase activity, the β-1,3- or β-1,6-glycosidic linkages of laminarin by using, as a substrate, laminarin, which is a polysaccharide of glucose made up of β-1,3-linked backbone with β-1,6-linked branches, thereby producing glucose alone. It was also confirmed that the Bgl1B protein had transglycosylase activity, and thus produced, from laminarin or laminaribiose, oligosaccharides having high degrees of polymerization by controlling the concentration of the enzyme and reaction time.

Therefore, the present invention provides a composition for producing glucose or a laminarioligosaccharide, including a β-glucosidase having the amino acid sequences of SEQ ID NO: 1, wherein the β-glucosidase has exo-type glucanase and transglycosylase activities.

The present invention also provides a method of producing glucose or a laminarioligosaccharide, including reacting a β-glucosidase having the amino acid sequences of SEQ ID NO: 1 with laminarin or laminaribiose to thereby produce glucose or a laminarioligosaccharide.

The β-glucosidase not only exhibits exo-type glucanase activity that enables the cleavage of the β-1,3- or β-1,6-glycosidic linkages of laminarin, but also exhibits transglycosylase activity against laminarin or laminaribiose.

In addition, the optimum pH of the β-glucosidase in a buffer may vary depending on the type of buffer, but the β-glucosidase exhibits an enzymatic activity of 80% or more at about pH 5 to about pH 7.5, and particularly, exhibits the highest activity at a pH of 6. In addition, the β-glucosidase exhibits an enzymatic activity of 80% or more at a pH of 6 and 10° C. to 40° C. However, at 50° C. or higher, the enzymatic activity is sharply reduced, and accordingly, since the β-glucosidase can cause a sufficient enzymatic reaction even at room temperature, there is an advantage that a production process can be economically performed without energy consumption for raising temperature. In addition, unlike existing enzymes, the enzyme may be inactivated even by heat treatment at a relative low temperature.

In addition, as a result of examining the effect of metal ions on the enzymatic activity of the β-glucosidase, $Mg^{2+}$, $Ni^{2+}$, and $Co^{2+}$ does not have a great influence on the enzymatic activity, whereas $Mn^{2+}$ inhibits enzymatic activity by about 50%, and $Cu^{2+}$ and $Fe^{2+}$ strongly inhibit enzymatic activity by about 10% or less.

The β-glucosidase may be derived from *Saccharophagus degradans* $2\text{-}40^T$, but the present invention is not particularly limited thereto.

In addition, the β-glucosidase may be transcribed and translated from a DNA fragment, i.e., a coding gene, associated with the production of a polypeptide not only including regions upstream and downstream of the coding region of the enzyme, but also including an intron between individual coding fragments. For example, the β-glucosidase may be transcribed and translated from the sequence set forth in SEQ ID NO: 2, but the present invention is not particularly limited. In addition, a protein having glucose or laminarioligosaccharide hydrolytic activity, as a mutation protein derived from the enzyme with one or more substitutions, deletions, translocations, additions, and the like, also falls within the scope of the enzyme of the present invention, and the protein preferably includes an amino acid sequence with at least 80% homology, at least 85% homology, at least 90% homology, at least 93% homology, at least 94% homology, at least 95% homology, at least 96% homology, at least 97% homology, at least 98% homology, and at least 99% homology, to the amino acid sequences set forth in SEQ ID NO: 1.

The β-glucosidase may be isolated and purified from a supernatant of a *Saccharophagus degradans* $2\text{-}40^T$ culture, or may be produced and isolated by using a strain other than *Saccharophagus degradans* $2\text{-}40^T$ by a genetic-engineering recombinant technique, or by an artificial chemical synthesis method or the like.

When the recombination technique is used, factors used to facilitate conventional recombinant protein expression, for example, an antibiotic resistance gene, and a reporter protein or peptide which can be used in affinity column chromatography, may be used, and this technique falls within the range that can be easily implemented by those of ordinary skill in the art to which the present invention pertains. For example, the β-glucosidase may be obtained from host cells transformed with a recombinant vector including a gene encoding the β-glucosidase, i.e., the nucleotide sequences set forth in SEQ ID NO: 2, or a culture thereof. The host cells may be *Escherichia coli*, but the present invention is not limited thereto.

The β-glucosidase may use, as a substrate, laminarin, laminaribiose, cellobiose, gentiobiose, lactose, agarobiose, or the like.

The β-glucosidase may produce glucose alone, or glucose and a laminarioligosaccharide by controlling reaction conditions.

The reaction conditions may be the concentration, reaction time, and the like of the β-glucosidase.

For example, glucose may be produced by reacting 0.1 U to 3 U of a β-glucosidase with laminarin (mg) as a substrate under conditions of 25° C. to 40° C. and 2 hours to 48 hours.

A laminarioligosaccharide may be produced by reacting 0.005 U to 0.05 U of a β-glucosidase with laminarin (mg) as a substrate or reacting 0.0001 U to 0.005 U of a β-glucosidase with laminaribiose (mg) as a substrate, under conditions of 2° C. to 40° C. and 2 hours to 72 hours.

The laminarioligosaccharide, which can be produced using laminarin or laminaribiose, may be any one of laminarioligosaccharides having degrees of polymerization (DP) of 2 or more, more particularly 2 to 10. More specifically, the laminarioligosaccharide may be laminaribiose (DP2), laminaritriose (DP3), laminaritetraose (DP4), laminaripentaose (DP5), laminarihexaose (DP6), or the like.

The degradation product of the β-glucosidase may be sequentially subjected to silica gel chromatography, which is adsorption chromatography, and biogel P2 chromatography, which is gel permeation chromatography, to isolate and purify glucose or a laminarioligosaccharide with a high purity of approximately 95%.

The "protein" and "polypeptide" as used herein are used interchangeably.

In the present invention, the expression "a polypeptide has a specific percentage (e.g., 80%, 85%, 90%, 95%, or 99%) of sequence identity with another sequence" means that, when two sequences are aligned and compared, the specific percentage of amino acid residues are the same. The alignment and percent homology or identity may be determined using suitable software programs known in the art, for example, those disclosed in the literature [CURRENT PROTOCOLS IN MOLECULAR BIOLOGY (F. M. Ausubel et al., (eds) 1987 Supplement 30 section 7.7.18)]. Preferable programs include the GCG Pileup program, FASTA (Pearson et al., 1988 *Proc. Natl Acad. Sci USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25:3389-3402). Another preferable alignment program is ALIGN Plus (Scientific and Educational Software, PA), preferably using basic parameters. Another available sequence software program is the TFASTA Data Searching Program available in Sequence Software Package Version 6.0 (Genetics Computer Group, University of Wisconsin, Madison, Wis.).

The term "recombinant" used herein means that, when being used in relation to a cell, nucleic acid, protein or vector, the cell, nucleic acid, protein or vector has been modified by introduction of a heterologous nucleic acid or protein or a change in a native nucleic acid or protein, or the cell is derived from a cell modified in such a manner. In other words, for example, a recombinant cell expresses a gene which is not found in a native (non-recombinant) form of the cell, or alternatively, expresses a native gene which is abnormally expressed or never expressed.

The "nucleic acid" as used herein encompasses single- or double-stranded DNA, RNA, and chemically-modified forms thereof. The "nucleic acid" and "polynucleotide" as used herein can be used interchangeably. Due to the degeneracy of the genetic code, one or more codons may be used to encode a specific amino acid, and the present invention encompasses a polynucleotide encoding a specific amino acid sequence.

The term "introduction" as used herein to describe the insertion of a nucleic acid sequence into a cell refers to "transfection," "transformation," or "transduction," and includes the description of incorporation of a nucleic acid sequence into a eukaryotic or prokaryotic cell. At this time, the nucleic acid sequence is incorporated into the genome of the cell (e.g., chromosomal, plasmid, plastid or mitochondrial DNA), and thus is converted into an autonomous replicon, or transiently expressed.

Hereinafter, the present invention will be described in further detail with reference to the following examples, but these examples are not intended to limit the scope of the present invention.

EXAMPLE

<Example 1> Overexpression and Purification of Bgl1B

To obtain the genomic DNA of *Saccharophagus degradans* 2-40$^T$ (ATCC43961), *Saccharophagus degradans* 2-40$^T$ was cultured in a minimal medium containing 2.3 g of instant ocean sea salt, 20 mM Tris-HCl, 2 g of glucose, 1 g of yeast extract, and 0.5 g of ammonium chloride per 1 L at 30° C. for 12 hours. The genomic DNA was extracted using a commercial DNA isolation kit (Qiagen, Valencia, Calif., USA). The target gene bgl1B was amplified from the genomic DNA by PCR. Primers used herein were 5'-ATA-CATATGAATAGACTTACACTACCGCCTTCTTCTCGT-3' (Forward: SEQ ID NO: 3) and 5'-ATAGCGGCCGCGCTCCTACTCGA-GACAAACTCAGCAAATGC-3' (Reverse: SEQ ID NO: 4). To purify the protein by affinity chromatography, the nucleotide sequence of a gene encoding 6 histidine residues at the C-terminus was added. The PCR product and a pET21α vector were digested with NdeI and NotI, respectively, and ligated to construct a pET21α-Bgl1B plasmid. The plasmid was transformed into *Escherichia coli* DH5α.

To overexpress the obtained gene, the gene was transformed into a protein-expressing host, *Escherichia coli* B121 (DE3). The cells were cultured in a Luria-Bertani (LB) broth containing 50 mg/L of ampicillin at 37° C. until absorbance at 600 nm reached 0.6. To induce protein expression, 0.1 mM IPTG was added and the induction temperature was set at 16° C., and a protein was allowed to be overexpressed in a water-soluble form for 16 hours. After culture, centrifugation was performed to recover the cells, the cells were released using a 20 mM Tris-HCl buffer (pH 7.4), and then disrupted by ultrasonication and centrifuged again to obtain a supernatant. The recombinant protein was purified using a HisTrap column (GE Healthcare, Piscataway, USA). The purified protein was concentrated using an Amicon Ultra Centrifugal filter (30,000 molecular weight cut-off; Millipore, Billerica, Mass., USA), and the concentration of the protein was measured using a bicinchoninic acid (BCA) protein assay kit (Thermo Fisher Scientific, San Hose, Calif., USA).

The molecular weight of the expressed Bgl1B was measured as 49.8 kDa using 8% SDS-PAGE (FIG. 1).

<Example 2> Confirmation of Optimum pH and Activation Temperature of Bgl1B Protein To investigate the pH for optimum activity of the Bgl1B protein, 20 mM sodium acetate (pH 4.0-6.0), 20 mM sodium phosphate (pH 6.0-7.0), and 20 mM Tris-HCl—NaCl (pH 7.0-9.0) buffer, which contained 0.1% (w/v) cellobiose, were allowed to react with the Bgl1B protein at 40° C. for 15 minutes.

Figure 2:
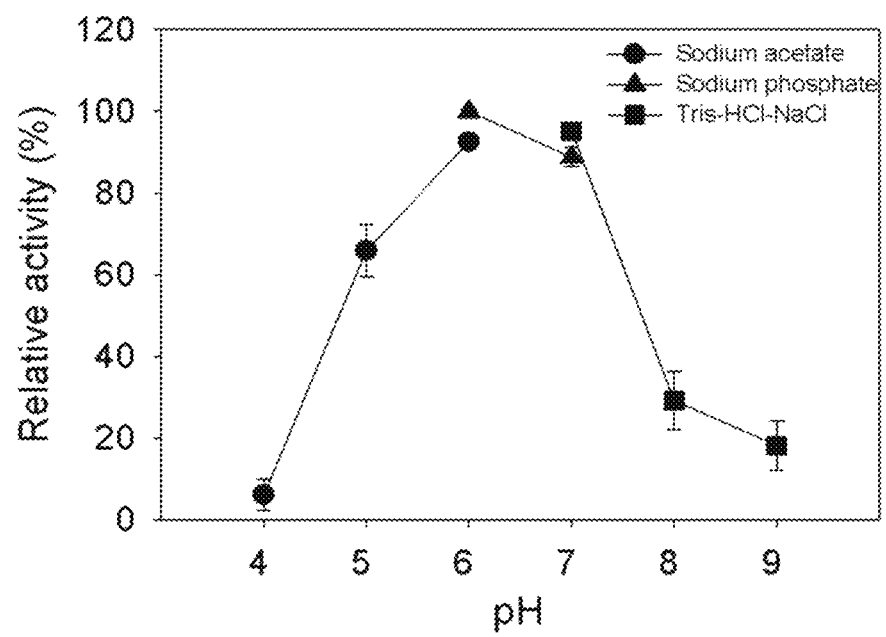
FIG. 2 illustrates results confirming the optimum activity pH of a β-glucosidase of the present invention.

FIG. 2 illustrates the relative activity of Bgl1B at a pH ranging from 4.0 to 9.0. Bgl1B exhibited the highest activity at a pH of 6. The activity was reduced to 30% or less at a pH of 4 and at a pH of 8 or higher.

Figure 3:
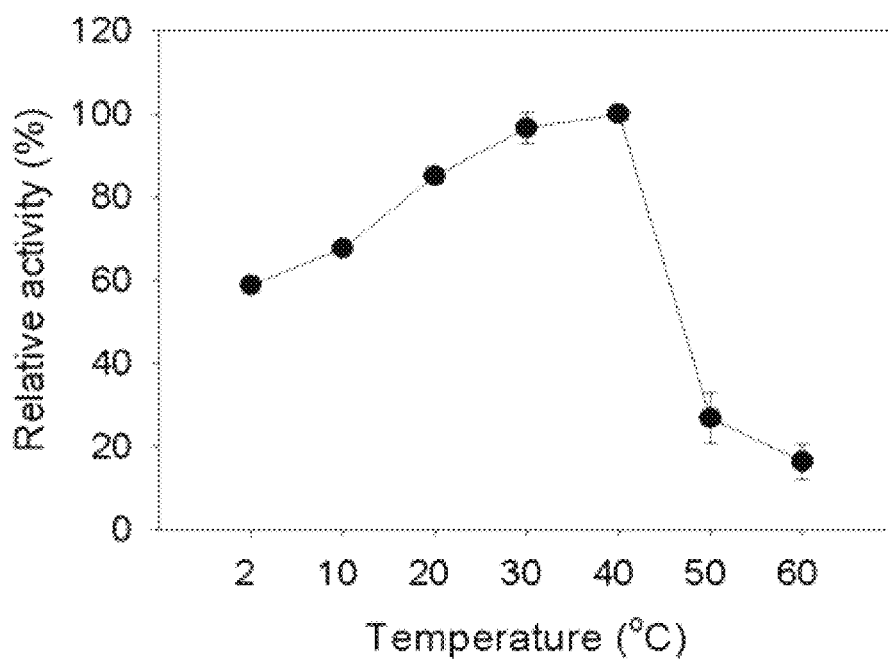
FIG. 3 illustrates results confirming the optimum temperature of a β-glucosidase of the present invention.

FIG. 3 illustrates the relative activity of Bgl1B at a temperature ranging from 2° C. to 60° C. At a pH of 6, Bgl1B exhibited the highest enzymatic activity at 40° C. An enzymatic activity of approximately 83% was maintained at 20° C. In addition, an enzymatic activity of 58% or higher was exhibited at a very low temperature, i.e., 2-10° C. However, the enzymatic activity was sharply reduced at 50° C. or higher. This indicates that an enzymatic reaction can be sufficiently performed even at room temperature, and thus an economical process may be performed without applying energy for raising temperature. In addition, the enzyme can be inactivated with only simple heat treatment.

Figure 4:
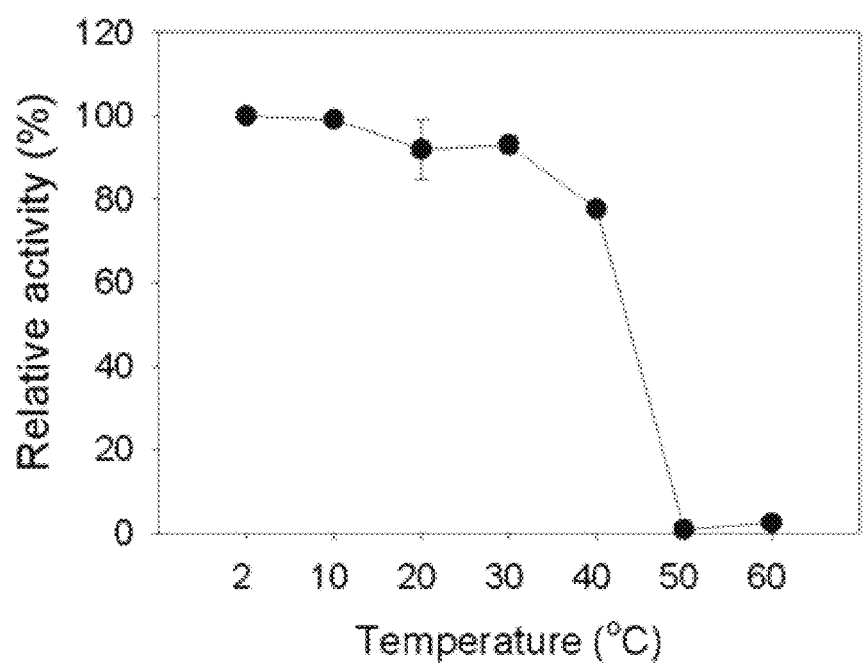
FIG. 4 illustrates results confirming the thermal stability of a β-glucosidase of the present invention.

FIG. 4 illustrates the stability with respect to temperature of the enzyme. After reaction at 40° C. for 1 hour, an enzymatic activity of 80% was maintained, and after reaction at 50° C. or higher for 1 hour, almost no activity was exhibited.

<Example 3> Effect of Metal Ions on Bgl1B

To examine the effect of metal ions on the activity of the Bgl1B protein, 10 mM $Mg^{2+}$, $Ca^{2+}$, $Mn^{2+}$, $Ni^{2+}$, $Cu^{2+}$, $Fe^{2+}$, and $Co^{2+}$ were added to 0.1% (w/v) cellobiose, and the relative activities of these cases were compared to the case where no metal ion was added.

As shown in Table 1, $Mg^{2+}$, $Ni^{2+}$, and $Co^{2+}$ did not have a great influence on enzymatic activity, but $Mn^{2+}$ exhibited an enzymatic activity of 56.2%. In addition, $Cu^{2+}$ and $Fe^{2+}$ exhibited very low enzymatic activity, i.e., 10%, which indicates a very strong inhibitory effect.

TABLE 1

| Metal ion | Relative enzymatic activity (%) |
| --- | --- |
| Control | 100.0 ± 2.8 |
| $Mg^{2+}$ | 98.9 ± 2.3 |
| $Ca^{2+}$ | 82.0 ± 1.5 |
| $Mn^{2+}$ | 52.6 ± 2.1 |
| $Ni^{2+}$ | 90.3 ± 2.7 |
| $Cu^{2+}$ | 0.0 ± 0.0 |
| $Fe^{2+}$ | 8.2 ± 0.3 |
| $Co^{2+}$ | 95.7 ± 1.6 |

<Example 4> Confirmation of Substrate Specificity of Bgl1B

To confirm the substrate specificity of the Bgl1B protein, each of 0.2% (w/v) of a plurality of disaccharides in a 20 mM sodium phosphate buffer (pH 6) was allowed to react with 0.6 U of Bgl1B for 1 hour. As substrates used, two groups were used: a first group including terrestrial-derived disaccharides, cellobiose (β-1,4 linkage), lactose (β-1,4 linkage), gentiobiose (β-1,6 linkage), sucrose (α-1,2 linkage), maltose (α-1,4 linkage), and mellibiose (α-1,6 linkage); and a second group of marine-derived substrates including laminaribiose (β-1,3 linkage), agarobiose (β-1,4 linkage), neoagarobiose, and agarotriose (β-1,6 linkage and α-1,4 linkage), which is a trisaccharide (α-1,4 linkage).

Figure 5:
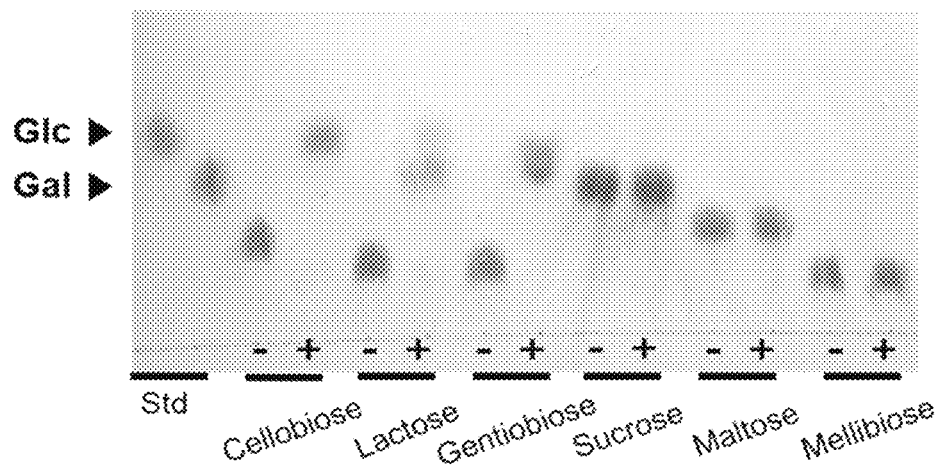
FIG. 5 illustrates TLC analysis results obtained by screening the substrate specificity of a β-glucosidase using various disaccharides as a substrate, wherein A of FIG. 5 shows terrestrial-derived disaccharides, and B of FIG. 5 shows marine-derived disaccharides.
Figure 5:
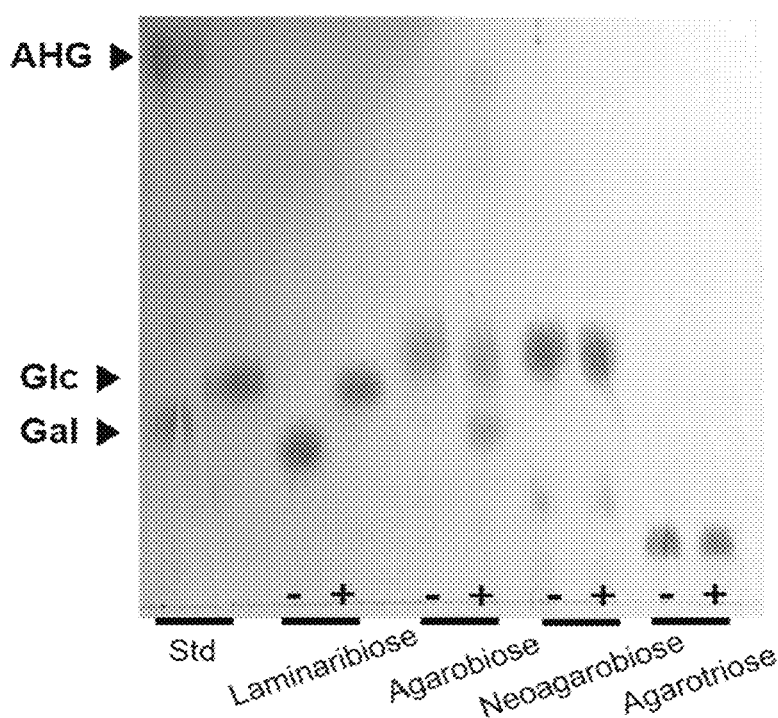

As shown in FIG. 5, Bgl1B was able to hydrolyze all disaccharides with β-linkages. In contrast, Bgl1B was unable to hydrolyze any disaccharide with an α-linkage. Bgl1B was also unable to hydrolyze agarotriose. Thus, it was confirmed that Bgl1B has a wide range of enzymatic activity which enables hydrolysis of disaccharides with β-linkages.

<Example 5> Confirmation of Enzymatic Reaction Rate of Bgl1B for Various Substrates To confirm the enzymatic reaction rate of the Bgl1B protein for various substrates, the Bgl1B protein was allowed to react with each substrate at various concentrations of 0.1-0.4% (w/v) at pH 6 and 40° C. $V_{max}$, $K_m$, and $k_{cat}$, which are parameters related to an enzymatic reaction rate, were determined from the Lineweaver-Burk plot.

TABLE 2

| Enzyme | Substrate | Glycosidic linkage | $V_{max}$ (U/mg protein) | $K_m$ (mM) | $k_{cat}$ (s$^{-1}$) | $k_{cat}/K_m$ (mM$^{-1}$s$^{-1}$) |
|---|---|---|---|---|---|---|
| Bgl1B | Laminaribiose | β-1,3 | $1.1 \times 10^2$ | $9.9 \times 10^{-1}$ | $9.1 \times 10^1$ | $9.2 \times 10^1$ |
| | Cellobiose | β-1,4 | $1.6 \times 10^1$ | $2.0 \times 10^1$ | $1.3 \times 10^1$ | $6.5 \times 10^{-1}$ |
| | Gentiobiose | β-1,6 | $1.1 \times 10^0$ | $1.3 \times 10^1$ | $8.8 \times 10^{-1}$ | $6.6 \times 10^{-2}$ |
| | Lactose | β-1,4 | $1.0 \times 10^0$ | $2.0 \times 10^1$ | $8.3 \times 10^{-1}$ | $4.1 \times 10^{-2}$ |
| | Agarobiose | β-1,4 | $3.1 \times 10^{-1}$ | $6.9 \times 10^1$ | $2.6 \times 10^{-1}$ | $3.7 \times 10^{-3}$ |
| Novozyme 188 | Laminaribiose | β-1,3 | $4.2 \times 10^{-1}$ | $2.5 \times 10^0$ | $8.5 \times 10^{-1}$ | $3.4 \times 10^{-1}$ |
| | Cellobiose | β-1,4 | $3.9 \times 10^0$ | $3.4 \times 10^0$ | $7.8 \times 10^0$ | $2.3 \times 10^0$ |

As shown in the results of Table 2, in a collective view of the parameters, Bgl1B exhibited the highest substrate specificity for laminaribiose. Compared to the commercialized enzyme Novozyme 188, Bgl1B exhibited a 259-fold greater $V_{max}$, a 2.5-fold lower $K_m$, and a 108-fold greater $k_{cat}$, showing 108-fold greater catalytic efficiency. After laminaribiose, Bgl1B has high substrate specificity in the order of cellobiose, gentiobiose, lactose, and agarobiose.

<Example 6> Confirmation of Characteristics of Enzymatic Reaction of Bgl1B Protein Using HPLC and TLC Characteristics of the enzymatic reaction of the Bgl1B protein using, as a substrate, laminarin, which is a polysaccharide, were analyzed using high performance liquid chromatography (HPLC) and thin layer chromatography (TLC). HPLC analysis was performed using Agilent 1100 HPLC equipped with a gel permeation and ligand exchange column (KS-802; Shodex) and a refractive index detector, and analysis conditions were a flow rate of 0.5 mL/min, a column temperature of 80° C., and sterile water as a mobile phase. For TLC analysis, 1 μl of a reaction product was loaded onto silica gel 60 plates (Merck), and then developed using a mixed solvent of n-butanol:acetic acid:water (volume ratio of 3:2:2), and treated with 10% (v/v) of sulfuric acid for visualization.

Figure 6A:
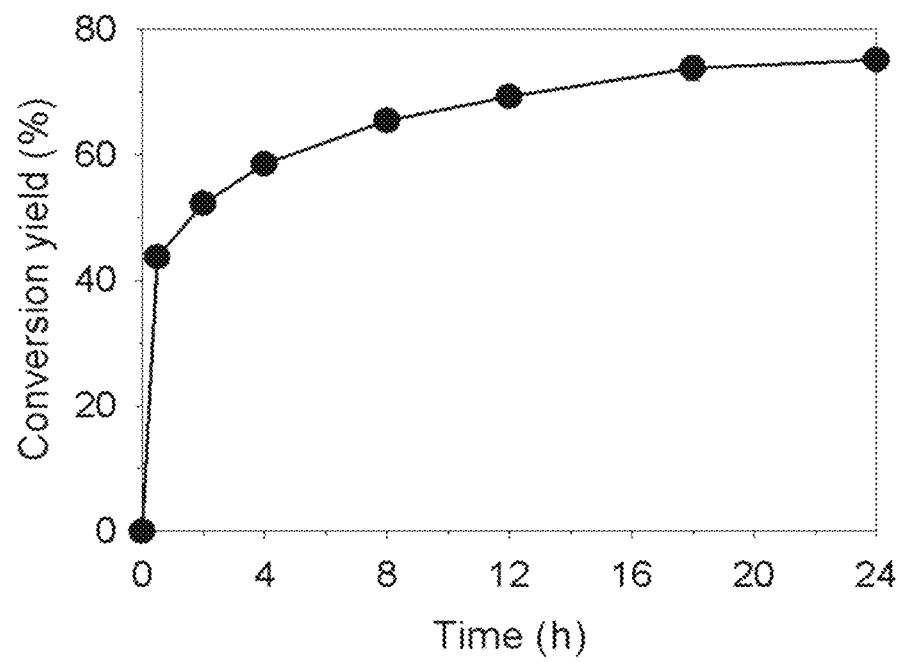
FIG. 6B illustrates HPLC analysis results of the major product.
Figure 6B:
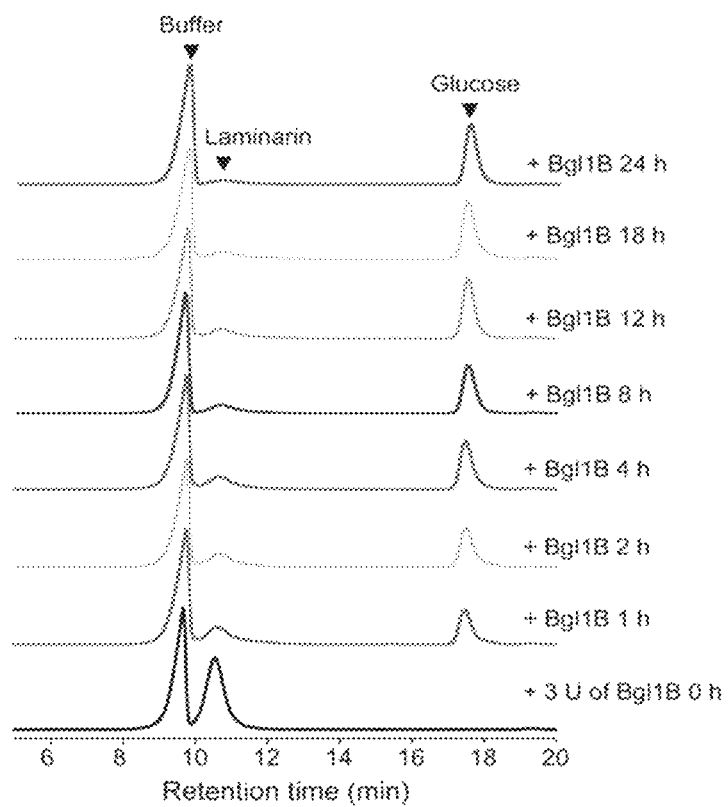

As a result of reacting 3 U of Bgl1B with 0.2% (w/v) of laminarin at 40° C. for 24 hours, as shown in FIG. 6A, a production yield of glucose from laminarin was very high, i.e., 75%, and as shown in FIG. 6B, it was confirmed by HPLC analysis that laminarin is degraded by Bgl1B and consequently, only glucose is produced without the production of oligosaccharides.

Figure 7A:
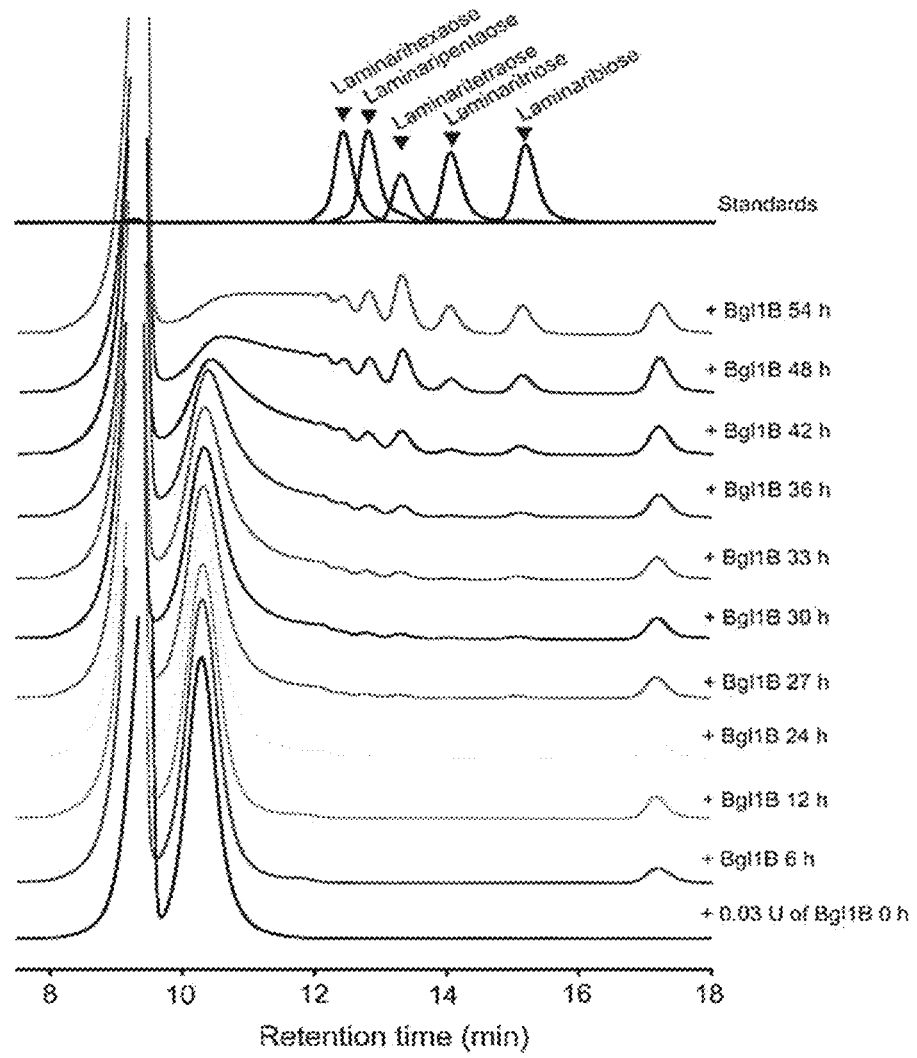
FIG. 7A illustrates HPLC analysis results of laminarioligosaccharides produced through transglycosylase activity against laminarin.
Figure 7B:
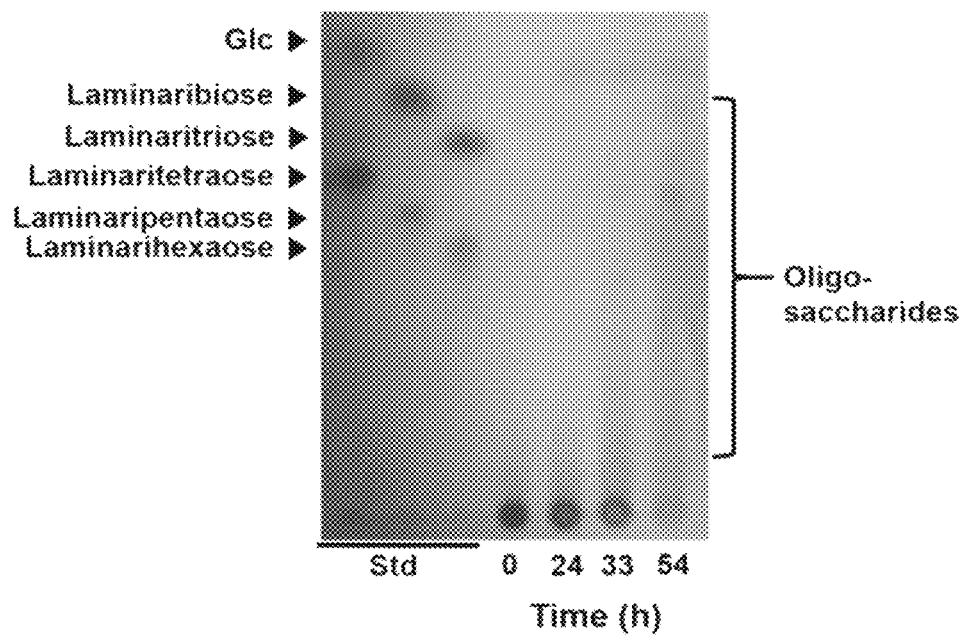
FIG. 7B illustrates TLC analysis results of the laminarioligosaccharides.

In addition, as a result of reacting Bgl1B at a very low concentration of 0.03 U with 0.2% (w/v) of laminarin by varying reaction conditions, as shown in FIGS. 7A and 7B, glucose was produced from laminarin up to 24 hours, after which the amount of glucose did not increase any longer and oligosaccharides with low degrees of polymerization such as DP2, DP3, and DP4 were produced. These results were also confirmed in the case of laminaribiose.

Figure 8A:
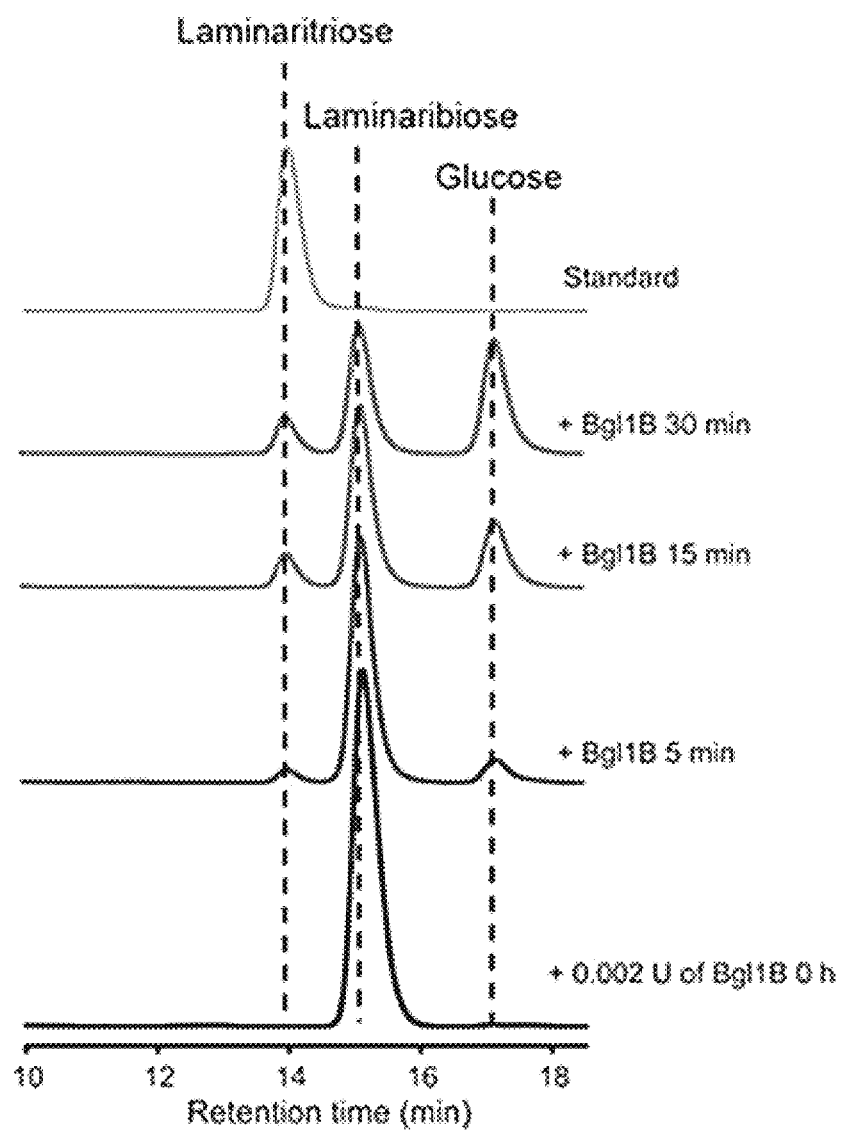
FIG. 8A illustrates HPLC analysis results of laminaritriose and glucose produced through transglycosylase activity against laminaribiose.

As a result of reacting 0.002 U of Bgl1B with 0.3% (w/v) of laminarin, as shown in FIGS. 8A and 8B, the production of DP3 was confirmed.

From these results, it was confirmed that Bgl1B alone can produce, as a major product, glucose, which is a fermentable sugar, from laminarin under desired conditions, and it was also confirmed that oligosaccharides, which are a functional material, are produced from laminarin and laminaribiose through transglycosylase activity.

The present invention can be applied to the field of production of glucose and a laminarioligosaccharide by an enzymatic reaction

What is claimed is:

1. A method of producing glucose and a laminarioligosaccharide, comprising reacting a β-glucosidase having the amino acid sequence of SEQ ID NO: 1 with laminarin to thereby produce glucose and a laminarioligosaccharide, wherein the reaction is performed by using 0.005 U to 0.05 U of a β-glucosidase per 1 mg of laminarin under conditions of 2° C. to 40° C. for 27 hours to 54 hours.

2. The method of claim 1, wherein the laminarioligosaccharide is any one of laminarioligosaccharides having degrees of polymerization of 2 to 10.

* * * * *